(12) United States Patent
Snyder et al.

(10) Patent No.: US 9,663,750 B2
(45) Date of Patent: May 30, 2017

(54) MANUFACTURING ARTICLE

(71) Applicant: Saint-Gobain Performance Plastics Corporation, Solon, OH (US)

(72) Inventors: Mitchell L. Snyder, Hope, MI (US); Clemens E. Zoellner, Bay City, MI (US); Thomas R. Nixon, Au Gres, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 38 days.

(21) Appl. No.: 14/713,592

(22) Filed: May 15, 2015

(65) Prior Publication Data

US 2015/0329812 A1 Nov. 19, 2015

Related U.S. Application Data

(60) Provisional application No. 61/994,461, filed on May 16, 2014.

(51) Int. Cl.
| | | |
|---|---|---|
| *B01L 3/00* | (2006.01) | |
| *C12M 1/12* | (2006.01) | |
| *C12M 3/00* | (2006.01) | |
| *C12M 1/00* | (2006.01) | |
| *B01L 9/06* | (2006.01) | |

(52) U.S. Cl.
CPC ............ *C12M 23/04* (2013.01); *B01L 3/563* (2013.01); *C12M 23/40* (2013.01); *C12M 23/54* (2013.01); *C12M 29/00* (2013.01); *B01L 9/06* (2013.01)

(58) Field of Classification Search
CPC ........... B01L 3/563; B01L 9/06; C12M 23/04; C12M 23/40; C12M 23/54; C12M 29/00
USPC ............. 141/9, 104, 236, 244; 206/139, 229
See application file for complete search history.

(56) References Cited

U.S. PATENT DOCUMENTS

| | | | |
|---|---|---|---|
| 2,535,114 A | | 12/1950 | Acton |
| 3,618,757 A | * | 11/1971 | Funkhouser ........... B65D 71/16 206/194 |
| 3,875,000 A | | 4/1975 | Kaneda |

(Continued)

FOREIGN PATENT DOCUMENTS

WO 2015175943 A1 11/2015

OTHER PUBLICATIONS

International Search Report for PCT Application No. PCT/US2015/031084 Dated Jul. 28, 2015.

(Continued)

*Primary Examiner* — Nicolas A Arnett
(74) *Attorney, Agent, or Firm* — Chi S. Kim; Abel Law Group, LLP

(57) ABSTRACT

A manufacturing article adapted for use in the production of pharmaceuticals comprising a tray comprising a base having a top surface; and a manifold extending from the top surface of the base, the manifold comprising a sidewall and an upper surface, the upper surface further comprising a channel, wherein, when viewed from the top surface, the base has an area, $A_B$, the upper surface of the manifold has an area $A_M$, and $A_B > A_M$, and wherein the base is adapted to support a plurality of vessels each adapted to contain a fluid.

20 Claims, 7 Drawing Sheets

(56) References Cited

U.S. PATENT DOCUMENTS

| | | | |
|---|---|---|---|
| 5,052,557 A * | 10/1991 | Contino | B65D 75/245 206/142 |
| 5,404,922 A * | 4/1995 | Sliter | A23G 9/28 141/234 |
| 5,702,672 A * | 12/1997 | DeWitt | B01J 19/0046 422/130 |
| 6,066,497 A | 5/2000 | Powell | |
| 6,290,265 B1 | 9/2001 | Warburton-Pitt et al. | |
| 6,458,104 B2 | 10/2002 | Gautsche | |
| 6,635,441 B2 | 10/2003 | Downs et al. | |
| 6,723,555 B2 | 4/2004 | Downs et al. | |
| 6,780,638 B2 | 8/2004 | Powell | |
| 7,143,893 B2 * | 12/2006 | Kelly | B65D 75/245 206/139 |
| 7,360,647 B2 * | 4/2008 | Ogg | B65D 5/28 206/139 |
| 7,562,787 B2 * | 7/2009 | Serrano | A47G 23/0208 206/139 |
| 7,644,683 B2 * | 1/2010 | Aronowicz | A01K 61/008 119/205 |
| 8,328,009 B2 * | 12/2012 | Stahl | B65D 1/243 206/139 |
| 8,424,923 B2 | 4/2013 | Inman, Jr. et al. | |
| 8,563,301 B2 | 10/2013 | Bargh | |
| 8,607,971 B2 * | 12/2013 | Stahl | B65D 1/243 206/139 |
| 2002/0086418 A1 * | 7/2002 | Powell | C12M 23/50 435/295.1 |
| 2002/0146818 A1 * | 10/2002 | Downs | C12M 23/42 435/294.1 |
| 2003/0157591 A1 * | 8/2003 | Downs | C12M 23/42 435/41 |
| 2004/0157322 A1 * | 8/2004 | Downs | C12M 23/42 506/26 |
| 2005/0150783 A1 * | 7/2005 | Ogg | B65D 5/28 206/193 |
| 2008/0169292 A1 * | 7/2008 | Serrano | A47G 23/0208 220/507 |
| 2009/0050066 A1 | 2/2009 | Aronowicz | |
| 2011/0003323 A1 * | 1/2011 | Bargh | C12M 23/42 435/29 |
| 2014/0137978 A1 * | 5/2014 | Dissanayake | B65B 3/003 141/1 |
| 2015/0031084 A1 | 1/2015 | Banta et al. | |

OTHER PUBLICATIONS

Bio-Simplex, Sampling Manifold Systems, www.biopharm.saint-gobain.com, 2009, 2 pages.

* cited by examiner

MANUFACTURING ARTICLE

CROSS-REFERENCE TO RELATED APPLICATION(S)

The present application claims priority from U.S. Provisional Patent Application No. 61/994,461, filed May 16, 2014, entitled "MANUFACTURING ARTICLE," naming inventors Mitchell L. Snyder, Clemens E. Zoellner, and Thomas R. Nixon, and said provisional application is incorporated by reference herein in its entirety for all purposes.

FIELD OF THE DISCLOSURE

The present disclosure relates to a manufacturing article, and more particularly to a manufacturing article adapted for use in the production of biological or biologically active substances.

RELATED ART

Biological or biologically active substances are produced using equipment. Cell cultures are often grown and cultured for use in biological products. For example, cell cultures are frequently grown and cultured for use in biopharmaceutical processing. These cultures can be stored in vessels, where they can be exposed to varying processes and environmental conditions allowing for cellular growth and development.

Many traditional cell culture devices and techniques are developed for large scale production of cell cultures. These devices and techniques may utilize roller bottles or the like and can occupy large spaces. During small batch cell culturing or sampling processes, a single technician can be tasked with handling and transporting the cultures and associated equipment between various equipment and areas of a laboratory.

While relatively small compared to large scale productions, small batch production and sampling operations may include upwards of 80 liters or more of culture containing fluids. Traditional manufacturing articles are not readily adapted to handle small batch production or sampling operations as they are either large and bulky or too small and unstable to accommodate and sufficiently hold sufficient volumes of fluid.

There continues to exist a need for improved articles adapted for use with biological or biologically active substances, specifically, in both small batch operations and during large scape sampling processes.

BRIEF DESCRIPTION OF THE DRAWINGS

Embodiments are illustrated by way of example and are not limited in the accompanying figures.

DETAILED DESCRIPTION

Figure 1:
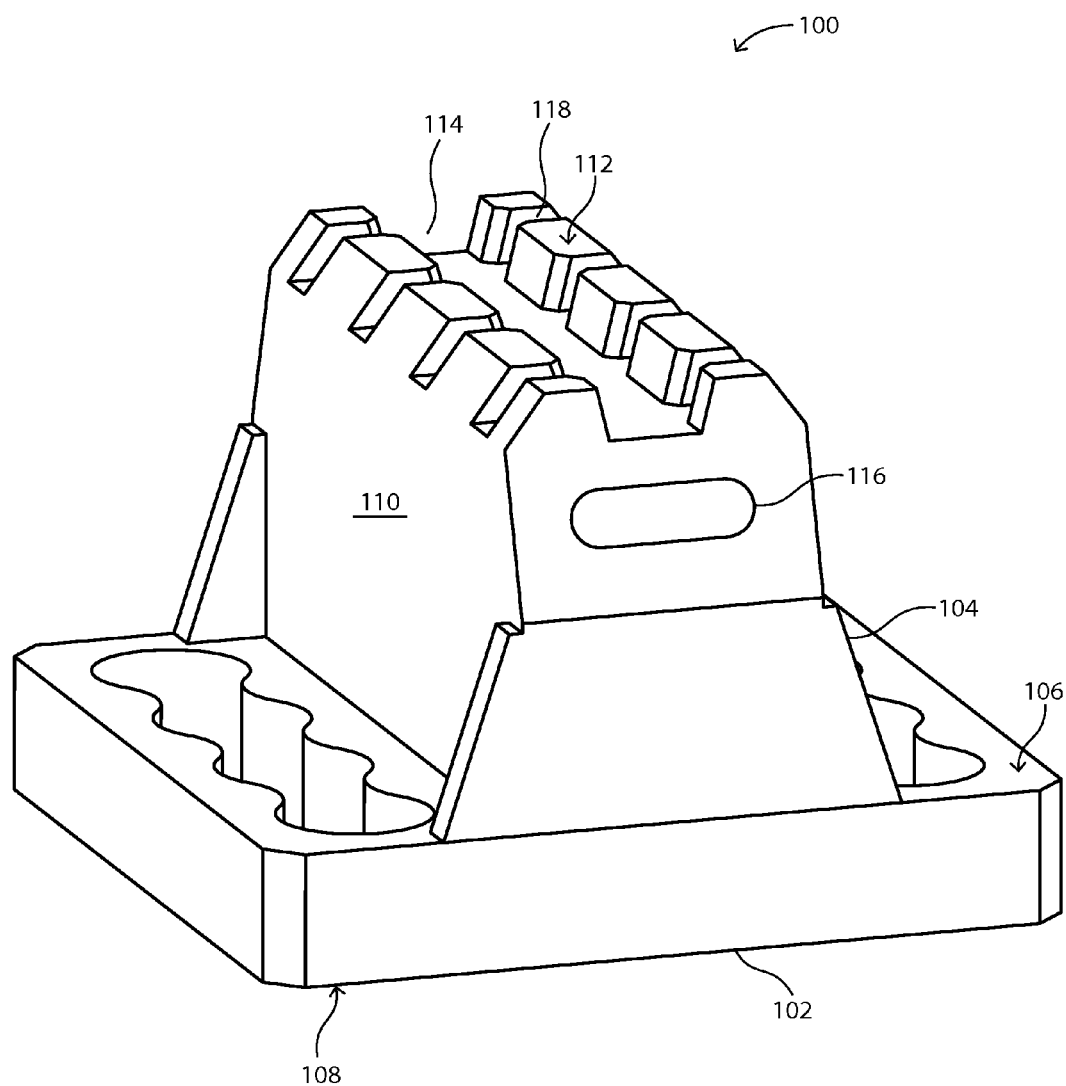
FIG. 1 includes a perspective view of a tray in accordance with an embodiment.

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

As used herein, the term "substantially" refers to a deviation of less than 5% of the value as described in the whole state, such as less than 4% of the value as described in the whole state, or even less than 2% of the value as described in the whole state. For example, the phrase "substantially devoid" may refer to a characteristic that is at least 95% devoid, such as at least 96% devoid, or even at least 98% devoid of that characteristic.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the biopharmaceutical processing arts.

A manufacturing article in accordance with one or more of the embodiments described herein can generally include a tray having a base defining a top surface and a manifold extending from the top surface of the base. In certain embodiments, the manifold can include a sidewall and an upper surface defining a channel. When viewed from the top surface of the base, the base can define an area, $A_B$, and the upper surface of the manifold can define an area, $A_M$. In accordance with one or more embodiments herein, $A_B$ can be greater than $A_M$.

A manufacturing article in accordance with one or more of the embodiments described herein can generally include a tray having a recess adapted to receive a plurality of vessels and individually support at least one vessel of the plurality of vessels. In a certain aspect, this can reduce the weight and size of the tray while simultaneously affording at least one vessel independent support, thereby allowing a user to transport large volumes of fluid within the vessels.

Referring initially to FIG. 1, a manufacturing article in accordance with embodiments described herein can generally include a tray 100 having a base 102 and a manifold 104. The base 102 can define a top surface 106 and a bottom surface 108 separated by a thickness, $T_B$. In a certain embodiment, the bottom surface 108 of the tray 100 can have a continuous, or nearly continuous, substantially flat surface spanning a length and width thereof. In another embodiment, the bottom surface 108 can be defined by a plane formed between or along portions of the tray that are adapted to contact, or rest against, a support surface, e.g., a table.

The manifold 104 can extend from the top surface 106 of the base 102, thereby defining a manifold sidewall 110 and an upper surface 112. In certain embodiments, the upper surface 112 of the manifold 104 can be parallel with the top surface 106 of the base 102. The manifold 104 can further define a channel 114 recessed from the upper surface 112 and extending toward the top surface 106 of the base 102. As discussed in greater detail below, the channel 114 can be adapted to receive at least a portion of a tube used to support and retain a fluid to and from a vessel disposed on the tray 100.

The manifold 104 can further define a plurality of sub-channels 118 recessed from the upper surface 112 and extending toward the top surface 106 of the base 102. Each sub-channel 118 can extend along a line that intersects the channel 114. In this regard, the channel 114 and sub-channels 118 can be in open communication. In particular embodiments, at least one of the sub-channels 118 can be oriented perpendicular to the channel 114. In yet more particular embodiments, all of the sub-channels can be oriented perpendicular to the channel 114. As discussed in greater detail below, each sub-channel can be adapted to receive at least a portion of a sub-tube used to transport a fluid to and from a vessel disposed on the tray 100.

As contemplated in particular embodiments disclosed herein, the tray 100 can at least partially comprise a polymer. Exemplary polymers can include, for example, a polyketone, a polyaramid, a polyimide, a polytherimide, a polyphenylene sulfide, a polyethersulfone, a polysulfone, a polypheylene sulfone, a polyamideimide, ultra high molecular weight polyethylene, a fluoropolymer, a polyamide, a polybenzimidazole, or any combination thereof. In a particular embodiment, the tray can comprise a high-density polyethelyne (HDPE).

Alternatively, and of particular significance during cell culturing, the tray 100 may be constructed at least partially from another material adapted to withstand temperatures of greater than 200° F., such as greater than 220° F., greater than 250° F., greater than 260° F., greater than 270° F., or even greater than 280° F., as the tray 100 may be subjected to these temperatures during processing and sampling. In this regard, a monolithic construction may increase resiliency by eliminating joints or other weakened locations that may deteriorate upon exposure to temperatures greater than 200° F.

In certain embodiments, an outer surface of the tray 100 can be generally smooth, for example, it is free from grooves, ripples, serrations, bumps, pitting, or any combination thereof. After reading this application, those skilled in the art will understand that surface roughness, such as caused during the normal manufacturing of the tray 100, constitutes "generally smooth" as used herein. In other embodiments, the outer surface of the tray can be smooth. The term "smooth" as used herein can generally refer to an enhanced surface finish, e.g., polished, buffed, etc. A smooth, or generally smooth, outer surface may reduce contaminant buildup along the outer surface of the tray, and in certain embodiments may increase sterility thereof.

In particular embodiments, an outer coating can be disposed along at least a portion of the outer surface of the tray. The outer coating can comprise a polymer, such as, for example, an elastomer. In particular embodiments, the outer coating can include an antimicrobial, antibacterial, or other contaminant reducing compound. The outer coating can have an outer surface that is smooth, or generally smooth, as discussed above in order to reduce contaminant building and increase sterility of the tray.

In a non-limiting embodiment, the tray 100 can be devoid, or substantially devoid, of right angled, or sharp, corners and edges. Rounded, chamfered, beveled, or even obtuse angles may instead be used along an outer surface of the tray to reduce buildup of contaminants and to reduce the likelihood that the tray can damage another component of the manufacturing article, e.g., a tube or sub-tube, during handling.

In particular embodiments, the tray 100 can be formed, for example, by injection molding, thermoforming, stamping, or otherwise shaped using any other similar known process or combination of processes for shaping. During the forming process, e.g., after completion of shaping, the tray may be sterilized to remove or destroy surface contamination. Exemplary sterilization techniques may include heat sterilization (e.g., steam sterilization, boiling water, dry heat), chemical sterilization (e.g., ethylene oxide, nitrogen dioxide, ozone, chlorine bleach, glutaraldehyde or formaldehyde, ortho-phthalaldehyde, hydrogen peroxide, peracetic acid, silver), radiation sterilization (e.g., ultraviolet light irradiation, ionizing radiation sterilization), or any combination thereof. In a preferred sterilization technique, sterility can be achieved using an autoclave for at least 15 minutes at 250° F. In such a manner, the tray may be essentially sterile, or sterile, in anticipation of usage. As used herein, "substantially sterile" refers to a sterility, e.g., a removal of transmissible agents such as fungi, bacteria, viruses, spore forms, etc., of no less than 90% as compared to an initial condition as measured prior to sterilization, while "sterile" refers to a sterility of no less than 99.9% as compared to an initial condition as measured prior to sterilization. After sterilization, the tray may be sealed or stored, e.g., in a sterile bag. This may reduce any recontamination of the tray.

As contemplated in a preferred embodiment herein, the tray 100 can be adapted for a single use. In this regard, a sealed tray 100 is utilized for no more than a single sampling or batch preparation process. After being used the tray 100 can be disposed. Alternatively, the tray 100 can be adapted for repeated use. In such a manner, the tray 100 may be subjected to resterilization between uses in an autoclave or other similar sterilization device.

In particular embodiments, the tray 100 can further include a handle 116 disposed along an outer surface thereof.

In an embodiment, the handle 116 can be disposed along an outer surface of the manifold 104, e.g., the sidewall 110. In another embodiment, the handle 116 can be disposed along an outer surface of the base 102 (e.g., FIGS. 2 and 3).

In a preferred embodiment, the handle 116 may be monolithically formed with the tray 100. For example, the handle 116 may include a recess extending into the tray 100. In such a manner, the overall weight of the tray 100 can be reduced. In alternate embodiments (not illustrated), the handle can include a hook, a clasp, a projection, or any other similar extension from the tray. Moreover, the handle can be independently formed and attached to the tray by a fastener, e.g., a threaded fastener, or an adhesive. In this regard, a traditional handle, e.g., a knob or U-shaped handle, can be engaged with the tray.

Figure 2:
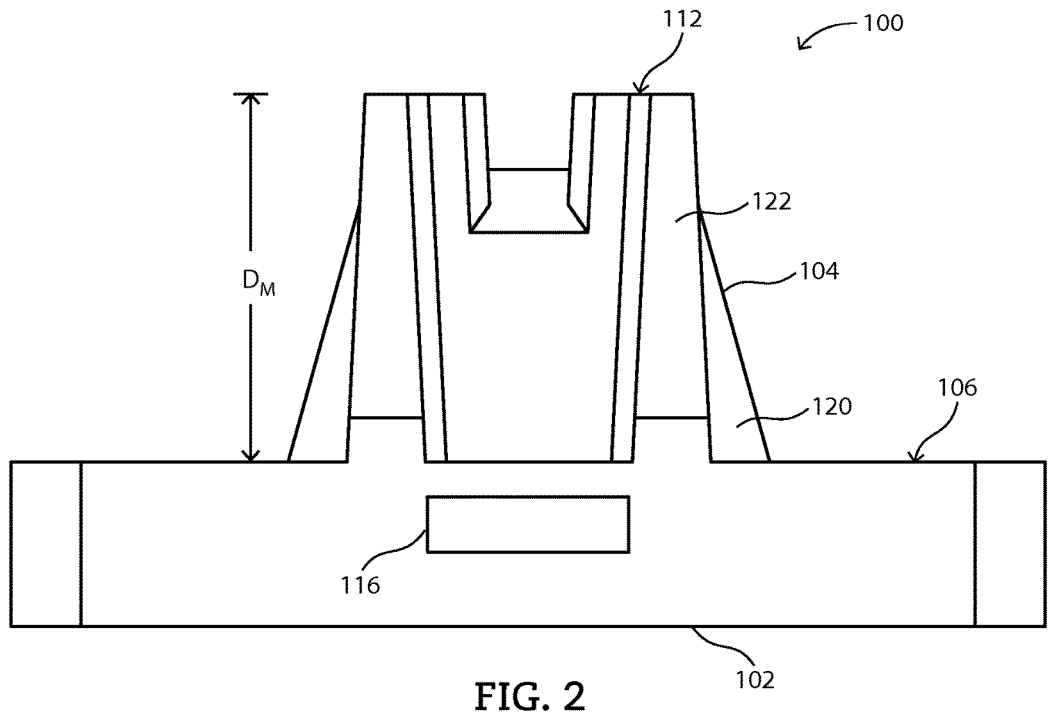
FIG. 2 includes a side view of a tray in accordance with an embodiment.
Figure 3:
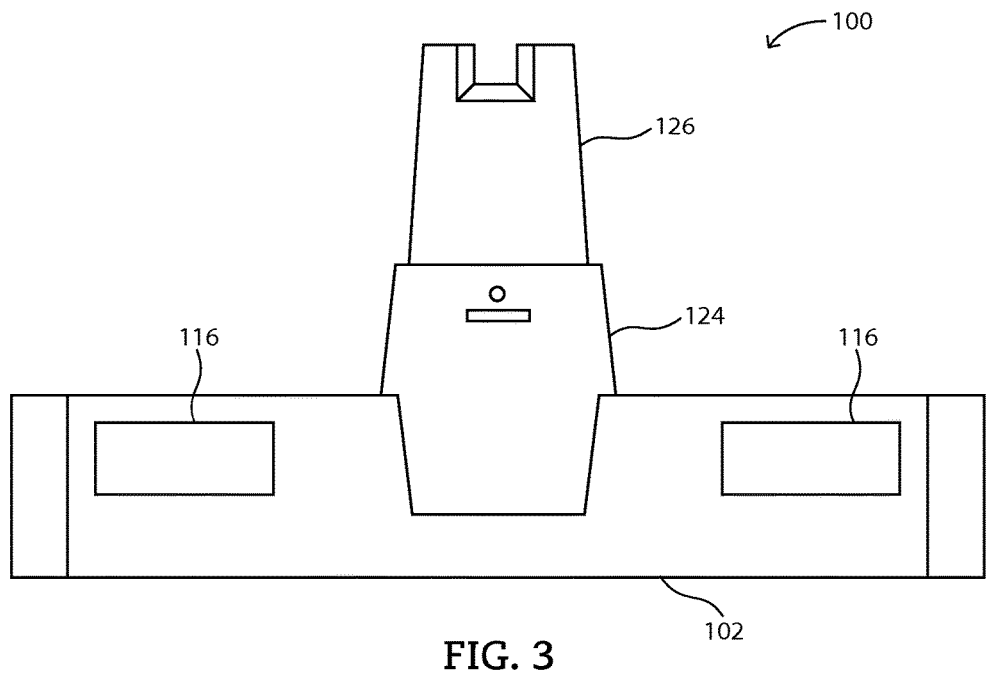
FIG. 3 includes a side view of a tray in accordance with an embodiment.

In a preferred embodiment, the tray 100 can include a plurality of handles 116, such as, for example, two handles, three handles, four handles, or even five handles. The handles 116 can be disposed at desirable locations around the outer surface of the tray 100, such as, for example, at opposite ends of the manifold 104. For example, as illustrated in FIG. 2, a single handle 116 can be disposed on each opposite side of the base 102 at a position below the manifold 104. Alternatively, as illustrated in FIG. 3, two handles 116 can be disposed on each opposite side of the base 102 at positions equally spaced apart from a centerline (not illustrated) of the manifold 104. Additionally, a person of ordinary skill in the art will understand that, while the handles 116 can be disposed at any location along the tray 100, it may be desirable to symmetrically position the handles 116 across a centerline of the tray 100 to enhance balance and stability during transportation of the tray.

Referring now to FIG. 2, the manifold 104 can extend from the top surface 106 of the base 102 a distance, $D_M$, as measured from the top surface 106 of the base 102 to the upper surface 112 of the manifold 104. In particular embodiments, $D_M$ can be greater than the thickness of the base, $T_B$. For example, $D_M$ can be greater than 1.25 $T_B$, such as greater than 1.5 $T_B$, greater than 1.75 $T_B$, greater than 2.0 $T_B$, greater than 2.25 $T_B$, greater than 2.50 $T_B$, greater than 2.75 $T_B$, or even greater than 3.0 $T_B$. Moreover, $D_M$ can be less than 100 $T_B$, such as less than 50 $T_B$, less than 10 $T_B$, less than 5 $T_B$, or even less than 3 $T_B$. In such a manner, $D_M$ can be within a range between and including 1.25 $T_B$ and 100 $T_B$, such as within a range between and including 1.5 $T_B$ and 50 $T_B$, within a range between and including 1.5 $T_B$ and 25 $T_B$, within a range between and including 1.75 $T_B$ and 10 $T_B$, within a range between and including 2.0 $T_B$ and 5 $T_B$, or even within a range between and including 2.25 $T_B$ and 3.0 $T_B$. Furthermore, $D_M$ can be within a range between and including any of the values described above. In a preferred embodiment, $D_M$ can be within a range of 1.0 $T_B$ and 3.0 $T_B$, thereby allowing an upwardly extending manifold with a relatively low center of gravity. After reading this application, a person of ordinary skill in the art will recognize that in an alternate embodiment $D_M$ can be less than $T_B$.

In particular embodiments, the sidewall 110 of the manifold 104 can be frustoconical. In such a manner, the sidewall 110 can taper from a wider bottom, coincident with the top surface 106 of the base 102, to a narrower dimension coincident with the upper surface 112 of the manifold 104. This can facilitate easier placement of a vessel along the base 102 of the tray 100 by providing an angled guiding surface which allows the vessel to be more easily placed in alignment with the base 102.

A reinforcement member 120 can be disposed along the sidewall 110 of the manifold 104 and may provide structural support thereto. In a further embodiment, the tray 100 can include a plurality of first reinforcement members 120 and a plurality of second reinforcement members 122. Each of the first reinforcement members 120 can have a height different than the height of the second reinforcement members 122. This may further enhance structural integrity of the tray 100 when transported by reducing torqueing forces and bending moments exhibited along the length and width of the tray 100. Specifically, as contemplated in particular embodiments herein, the reinforcement members 120 or 122 can assist in transmitting acute bending moments and torqueing loads exhibited along the base 102 into the manifold 104. This may allow transmission of loading conditions throughout the tray, resulting in a stiffer user feel.

As illustrated in FIG. 3, in yet more particular embodiments, the sidewall 110 of the manifold 104 can have at least two tiers 124 and 126. The tiers 124 and 126 can have any suitable stepped configuration adapted to correspond with a vessel (not illustrated) or to permit easier engagement of the vessel with the tray 100. Additionally, as discussed above, a tiered manifold can facilitate a stiffer base 102 by forming pleats which can spread torqueing and bending moments throughout the tray 100.

Figure 4:
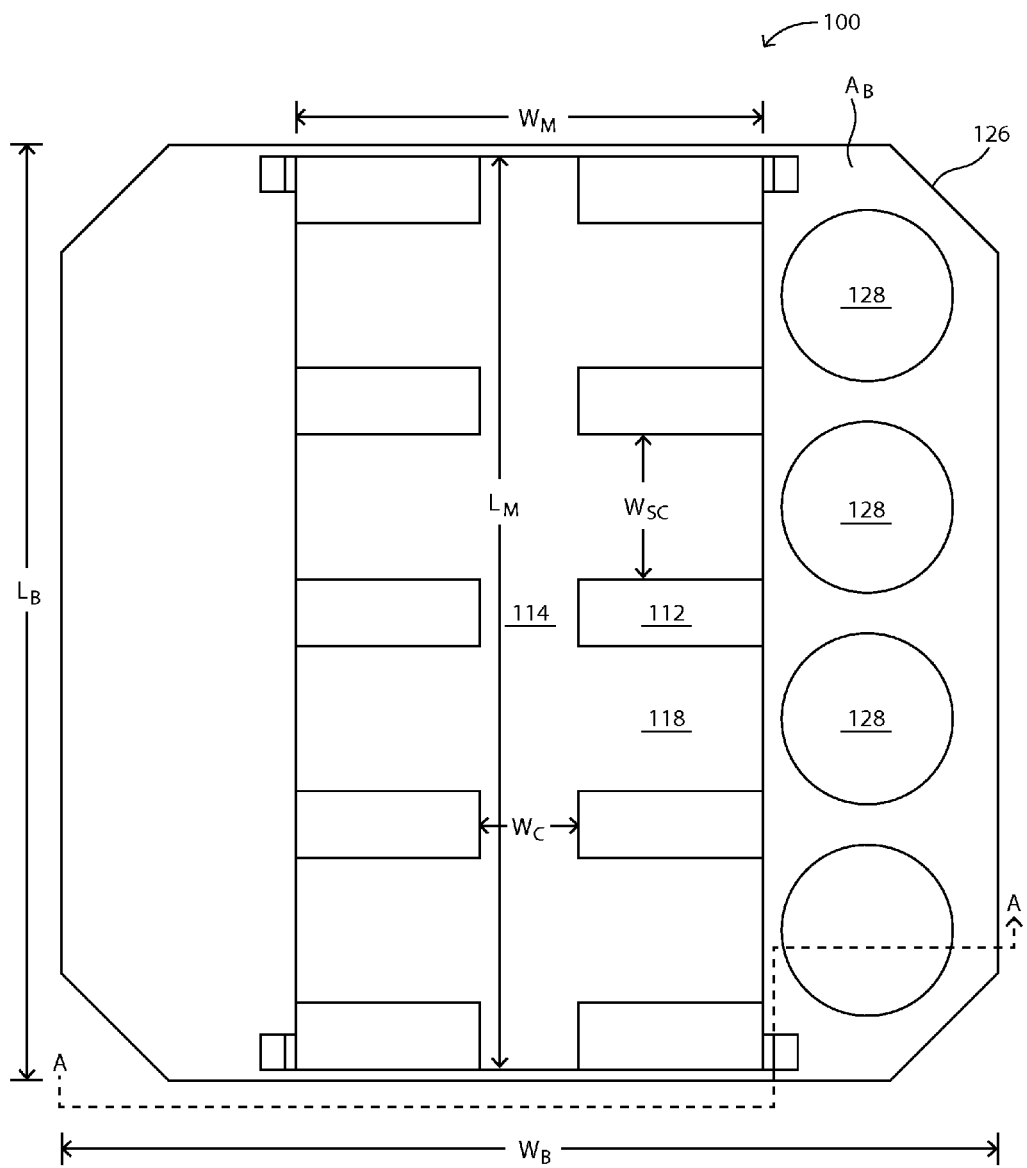
FIG. 4 includes a top view of a tray in accordance with an embodiment.

Referring now to FIG. 4, the upper surface 112 of the manifold 104 can define a surface area, $A_M$, as calculated by a product of a length, $L_M$, of the manifold and a width, $W_M$ of the manifold. The base 102 can define a surface, $A_B$, as calculated by a product of the length, $L_B$, of the base 102 and the width, $W_B$, of the base 102, minus an area of any cutout portions, e.g., corner cutout portions 126.

In a particular embodiment, $L_M$ can be greater than $W_M$, such as $L_M$ can be greater than 1.1 $W_M$, greater than 1.2 $W_M$, greater than 1.5 $W_M$, greater than 1.75 $W_M$, or even greater than 2.0 $W_M$. In another embodiment, $L_M$ can be less than 5.0 $W_M$, such as less than 4.0 $W_M$, or even less than 3.0 $W_M$. In particular embodiments, $A_B$ can be greater than $A_M$. For example, $A_B$ can be within a range between and including 1.1 $A_M$ and 5.0 $A_M$, 1.2 $A_M$ and 4.9 $A_M$, 1.3 $A_M$ and 4.8 $A_M$, 1.5 $A_M$ and 4.5 $A_M$, 2.0 $A_M$ and 4.0 $A_M$, or even within a range between and including 2.5 $A_M$ and 3.5 $A_M$.

The channel can define an average width, $W_C$, as measured along the upper surface 112 of the manifold 104. In a particular embodiment, $W_C$ can be less than $W_M$, such as no greater than 0.99 $W_M$, no greater than 0.75 $W_M$, no greater than 0.5 $W_M$, no greater than 0.25 $W_M$, or even no greater than 0.1 $W_M$. In another embodiment, $W_C$ can be no less than 0.01 $W_M$, such as no less than 0.05 $W_M$. Moreover, $W_C$ can be within a range between and including any of the values described above, such as, for example, between 0.15 $W_M$ and 0.30 $W_M$. In certain embodiments the channel width, $W_C$, can be constant along a length of the channel 114. In alternate embodiments, the channel width, $W_C$, can vary as a function of location. For example, in a non-limiting embodiment, $W_C$ may be greatest at, or near, a center point of the channel. A non-constant width may facilitate greater security of the tubes within the channel 114.

In particular embodiments, the channel 114 can generally extend along the length, $L_M$, of the manifold 104. In more particular embodiments, a centerline of the channel 114 can extend substantially parallel to the length of the manifold 104.

As illustrated in FIG. 4, the sub-channels 118 can each define a width, $W_{SC}$. As illustrated in FIG. 4, in particular embodiments, $W_{SC}$ can be greater than $W_C$. In such a manner, the sub-channels can permit a user to more easily maneuver sub-tubes (discussed in greater detail below) to respective vessels.

In other embodiments, $W_{SC}$ can be no greater than $W_C$. In more particular embodiments, $W_{SC}$ can be less than $W_C$. For example, $W_{SC}$ can be less than 0.99 $W_C$, such as less than 0.9 $W_C$, or even less than 0.75 $W_C$. As described below, because the tubes in the sub-channels have proportionately less volumetric flow as compared to the tube in the channel, the dimensions of the sub-channel can be smaller than the dimensions of the channel. The combination of channels and sub-channels along the upper surface 112 of the manifold 104 can create a castellated upper surface 112 of the manifold 104.

Figure 5:
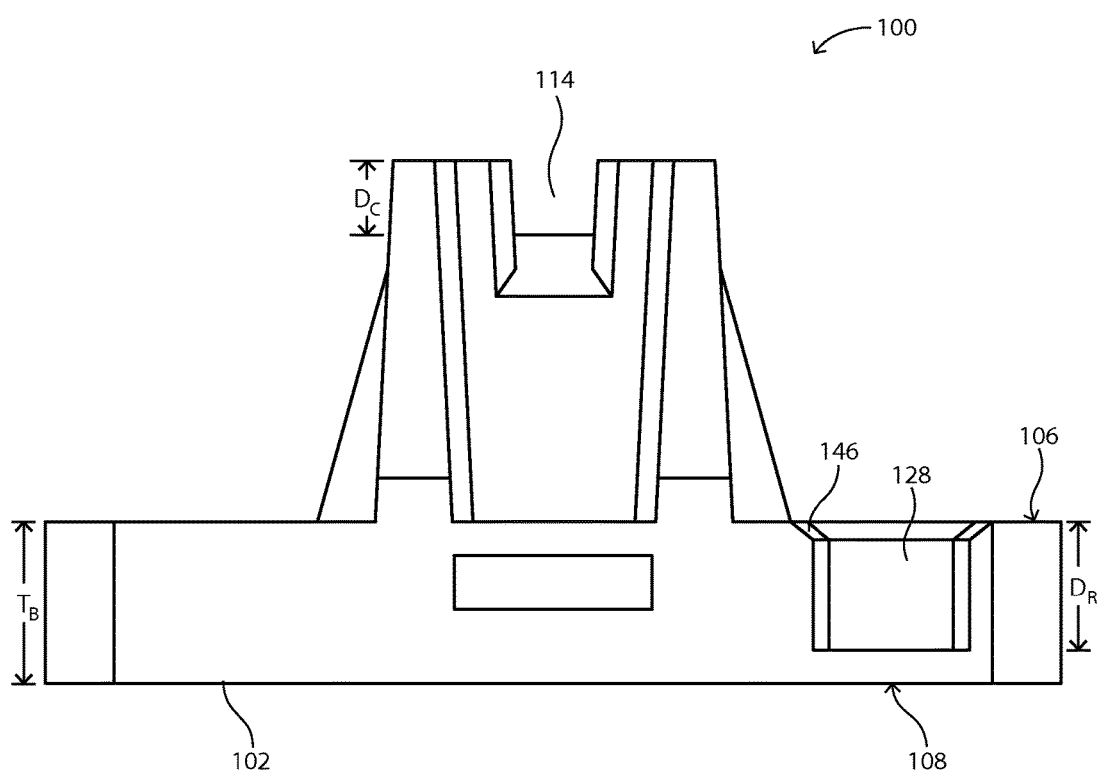
FIG. 5 includes a partial cross-sectional side view of a tray in accordance with an embodiment, as seen along Line A-A in FIG. 4.

Referring still to FIG. 4, in particular embodiments the tray 100 can further include at least one recess 128 adapted to receive at least one vessel (not illustrated). As illustrated in FIG. 5, the at least one recess 128 can be disposed on the base 102 of the tray 100 extending from the top surface 106 in a direction toward the bottom surface 108.

Figure 6:
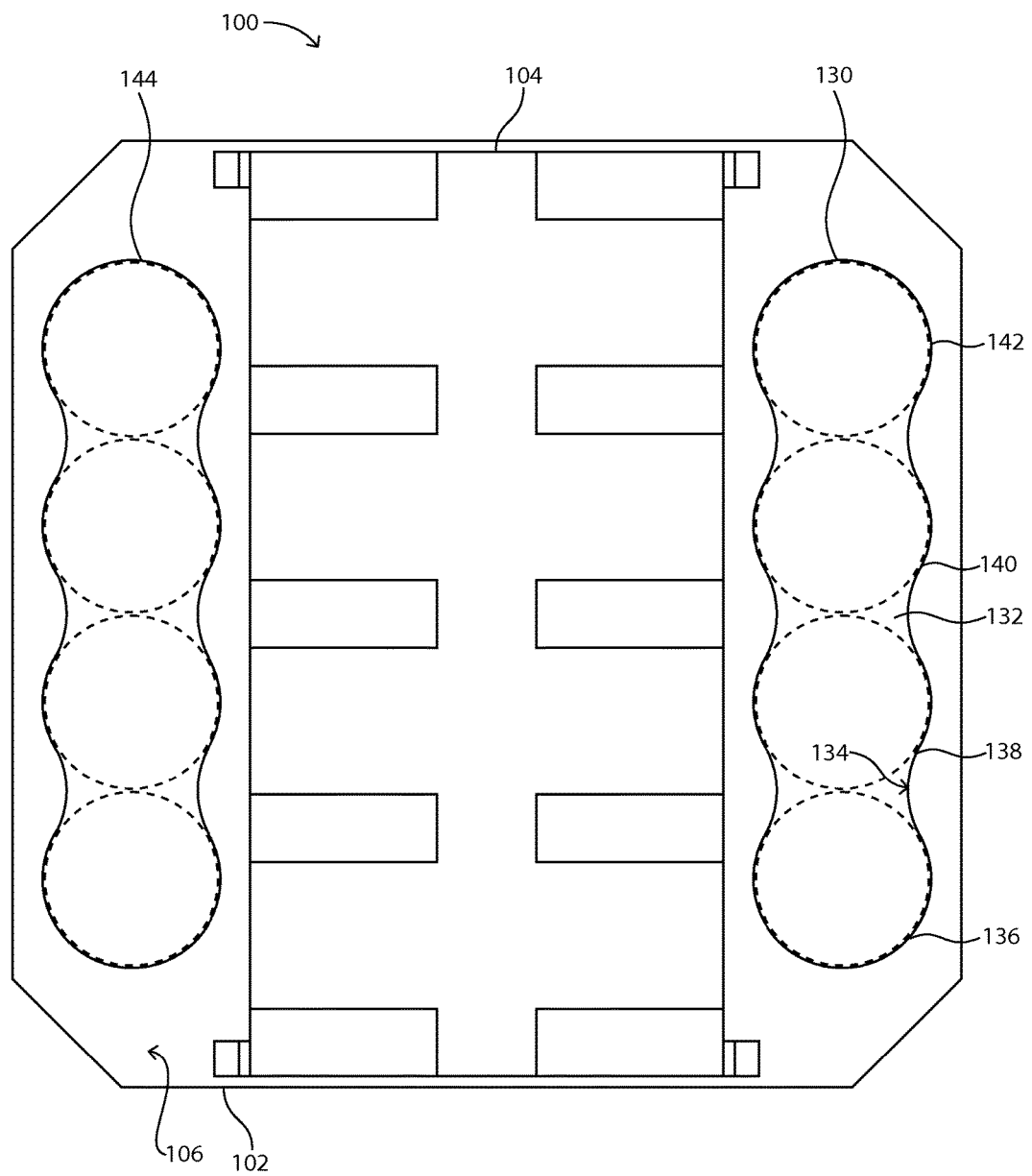
FIG. 6 includes a top view of a tray in accordance with an embodiment.

Referring now to FIG. 6, in a preferred embodiment, the tray 100 can include a recess 130 adapted to receive a plurality of vessels and individually support at least one vessel of the plurality of vessels. As used herein, "individually support" refers to a sidewall having sufficient lateral support, as measured in a direction parallel to the top surface 106 of the base 102, such that a vessel disposed within the recess is prevented from tipping, or rotating, about an axial length thereof, independent of whether a second vessel is disposed adjacent thereto. In other words, lateral support of a first vessel is not solely provided by a second vessel positioned directly adjacent to the first vessel.

In certain embodiments, the recess 130 can define a bottom wall 132 and a sidewall 134. When viewed from a top view, the sidewall 134 can define an undulating profile defining a maximum width, as measured between opposite sides of the recess 130, and a minimum width, as measured between opposite sides of the recess 130. In particular embodiments, the maximum width of the sidewall can be at least 1.1 times the minimum width of the sidewall, such as at least 1.25 times the minimum width of the sidewall, or even 1.75 times the maximum width of the sidewall.

The undulating sidewall 134 of the recess 130 can further define a plurality of discrete containment regions, e.g., a first discrete containment region 136, a second discrete containment region 138, a third discrete containment region 140, and a fourth discrete containment region 142. Adjacent discrete containment regions, e.g., 136 and 138, can be in open communication with each other and each adapted to receive one vessel.

The undulating sidewall 134 can be shaped and sized to accommodate vessels as necessary. For example, the first and second discrete containment regions 136 and 138 can house a first vessel and a second vessel, respectively. The first and second vessels can be aligned within the first and second discrete containment regions 136 and 138 such that a closest distance between the first and second vessels is no greater than 1 inch, such as no greater than 0.75 inches, no greater than 0.5 inches, or even no greater than 0.25 inches. In a further embodiment, adjacent discrete containment regions can be aligned such that the first and second vessels are in contact or immediately adjacent at a point location or along a plane.

In further embodiments, the tray 100 can include two recesses, the recess 130 and a recess 144. The recesses 130 and 144 can each be disposed on an opposite side of the manifold 104 along the base 102 of the tray 100. In certain embodiments, the recess 144 can be substantially identical to the recess 130, e.g., the recess 144 can define a maximum and minimum sidewall width equal to the maximum and minimum sidewall widths of the recess 130.

Referring again to FIG. 5, the recess(es) 130 or 144 can have a depth, $D_R$, as measured from the top surface 106 of the base 102 in a direction perpendicular thereto. In the case the recess(es) have rounded or otherwise non-planar bottom walls, the depth, $D_R$, of the recess(es) can be a maximum depth of the recess as measured from the top surface of the base to a bottom inner apex of the recess. In a particular embodiment, $D_R$ can be less than the thickness of the base, $T_B$. For example, in specific embodiments, $D_R$ can be less than 0.99 $T_B$, such as less than 0.95 $T_B$, less than 0.90 $T_B$, or even less than 0.75 $T_B$. Moreover, in further embodiments, $D_R$ can be no less than 0.05 $T_B$, such as no less than 0.1 $T_B$, no less than 0.2 $T_B$, or even no less than 0.25 $T_B$. $D_R$ can also be within a range between and including any of the values described above. In a preferred embodiment, $D_R$ is between 0.75 $T_B$ and 0.99 $T_B$, or more particularly, between 0.85 TB and 0.95 $T_B$. In this preferred embodiment, the recess can provide lateral support to a vessel while maintaining structural rigidity.

The recess(es) 130 or 144 can further define a lip 146 extending around a periphery thereof and joining the sidewall 134 with the top surface 106 of the base 102. In particular embodiments, the lip 146 can be chamfered. This can facilitate easier insertion of a vessel into the recess and provide an insertion tolerance to a user.

Referring still to FIG. 5, the channel 114 of the tray 100 can have a depth, $D_C$, as measured from the upper surface 112 of the manifold 104. In the case the channel 114 has a rounded or otherwise non-planar bottom wall, the depth, $D_C$, can be a maximum depth of the channel as measured from the upper surface 112 of the manifold 104 to an inner bottom apex of the channel 114. In accordance with embodiments described herein, $D_C$ is less than $D_M$. For example, $D_C$ can be no greater than 0.99 $D_M$, such as no greater than 0.75 $D_M$, no greater than 0.5 $D_M$, no greater than 0.25 $D_M$, or even no greater than 0.1 $D_M$. In further embodiments, $D_C$ can be no less than 0.01 $D_M$, or even no less than 0.05 $D_M$. Moreover, $D_C$ can be within a range between and including any of the values described above. Of significance, $D_C$ need only be sufficiently large to at least partially receive a tube extending therethrough. In this regard, in a preferred embodiment, $D_C$ is no less than 0.25 times the diameter of the tube, such as no less than 0.5 times the diameter of the tube, or even no less than 0.75 times the diameter of the tube. Moreover, in a further embodiment, $D_C$ can be sufficiently large to receive the entire diameter of the tube.

Figure 7:
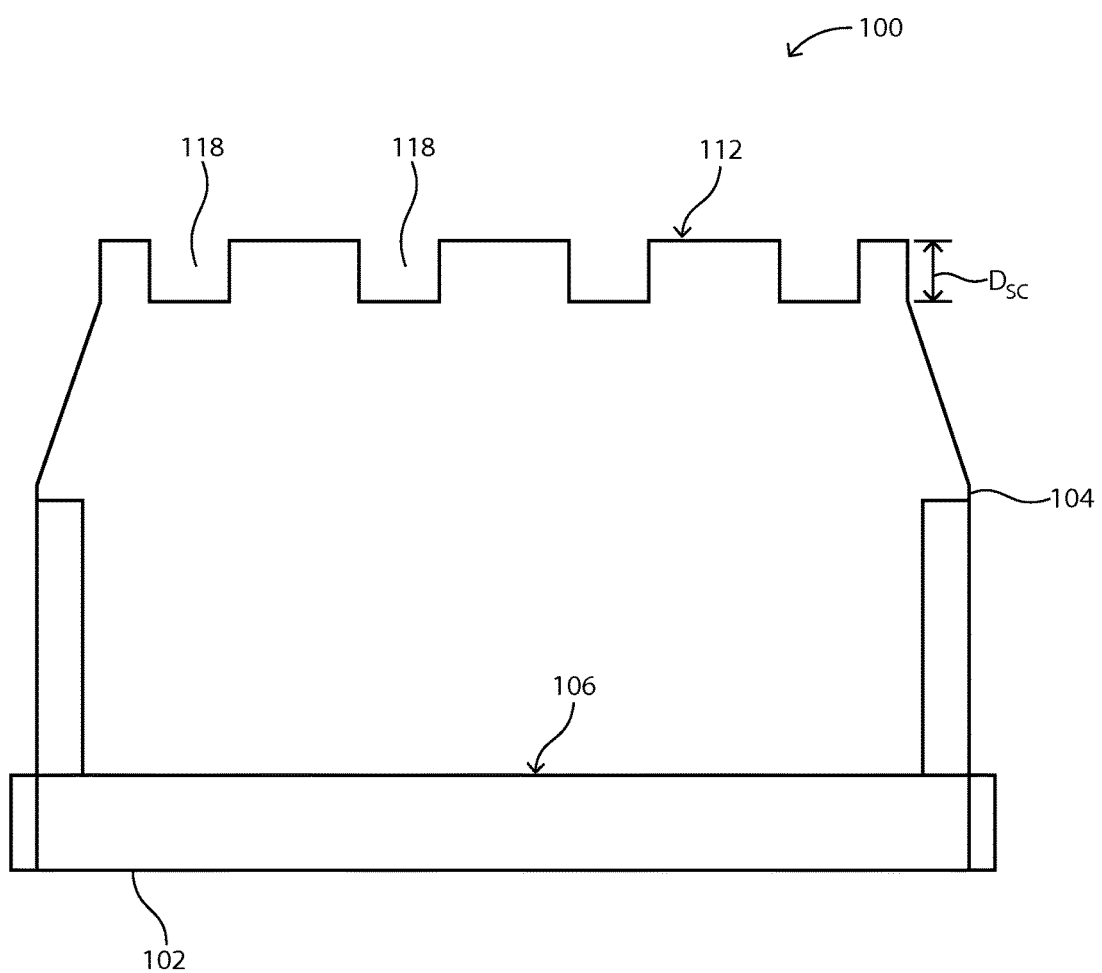
FIG. 7 includes a side view of a tray in accordance with an embodiment.

Referring now to FIG. 7, the sub-channels 118 can each have a depth, $D_{SC}$, as measured from the upper surface 112 of the manifold 104 in a direction toward the top surface 106 of the base 102, that is less than $D_C$. In the case the sub-channels 118 have a rounded or otherwise non-planar bottom wall, the depth, $D_{SC}$, can be a maximum depth of the sub-channels 118 as measured from the upper surface 112 of the manifold 104 to a bottom apex of the sub-channels 118. In particular embodiments, $D_{SC}$ can be equal to $D_C$. In other embodiments, $D_C$ can be greater than $D_{SC}$. For example, $D_C$ can be at least 1.01 $D_{SC}$, such as at least 1.1 $D_{SC}$, at least 1.2 $D_{SC}$, at least 1.3 $D_{SC}$, or even at least 1.5 $D_{SC}$. In further embodiments, $D_C$ can be no greater than 10 $D_{SC}$, such as no greater than 9 $D_{SC}$, no greater than 8 $D_{SC}$, no greater than 5 $D_{SC}$, or even no greater than 2 $D_{SC}$. Moreover, $D_{SC}$ can be within a range between and including any of the values described above. Of significance, $D_{SC}$ need only be sufficiently large to at least partially receive a sub-tube extending therethrough. In this regard, in a preferred embodiment, $D_{SC}$ is no less than 0.25 times the diameter of the sub-tube, such as no less than 0.5 times the diameter of the sub-tube, or even no less than 0.75 times the diameter of the sub-tube. Moreover, in a further embodiment, $D_{SC}$ can be sufficiently large to receive the entire diameter of the sub-tube.

Figure 8:
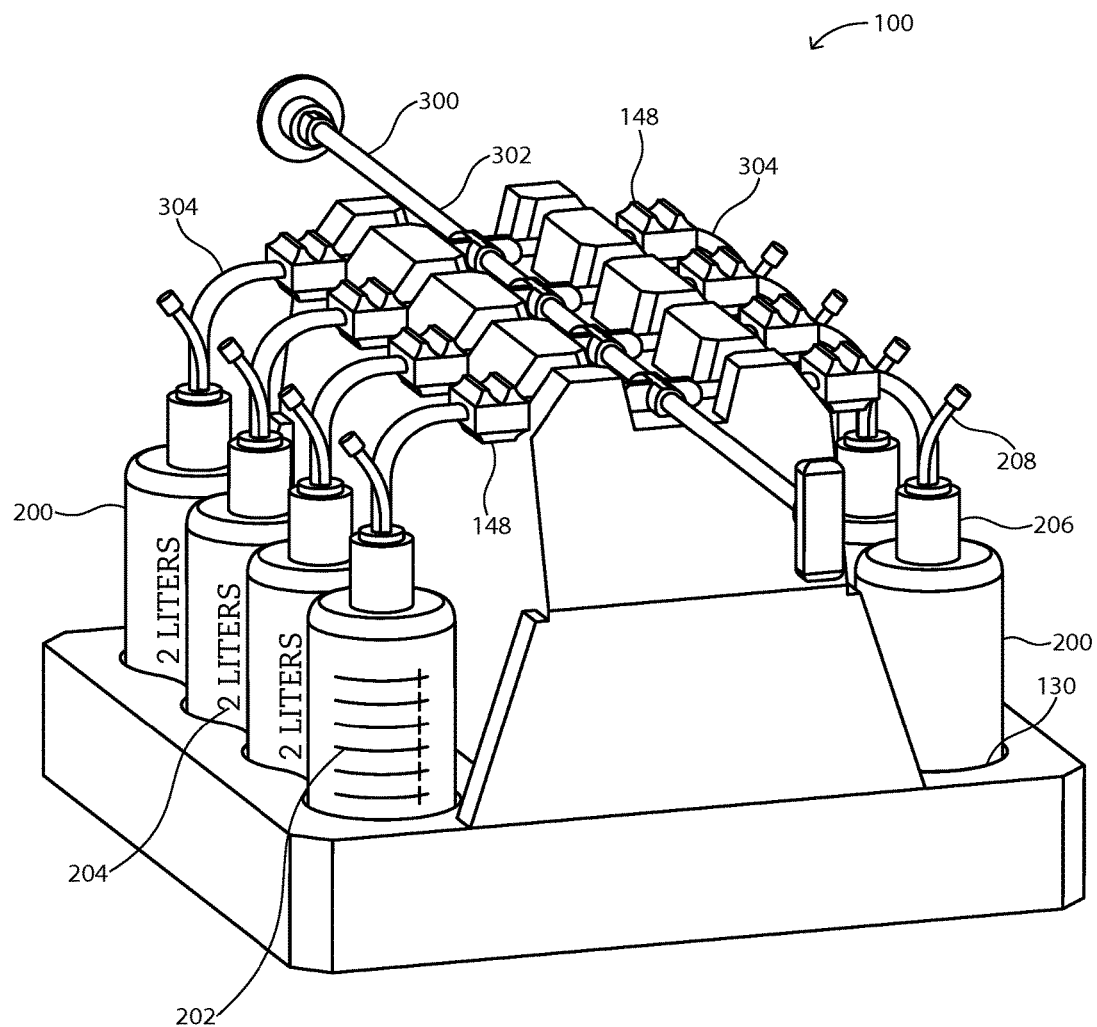
FIG. 8 includes a perspective view of a manufacturing article including a tray, a vessel and a tube assembly in accordance with an embodiment.

Referring to FIG. 8, the tray 100 can receive and support at least one vessel 200 in the recess 130 thereof. In particular embodiments, at least a portion of the vessel 200 can be frustoconical. In further embodiments, at least a portion of the vessel 200 can be cylindrical. In yet further embodiments, when viewed from a top view, at least a portion of the vessel 200 can be polygonal, e.g., triangular, quadrilateral, pentagonal, hexagonal, heptagonal, octagonal, etc. This may increase vessel integrity and prevent collapse thereof.

In certain embodiments, the vessel 200 can comprise a polymer, such as an inert polymer adapted to contact a biopharmaceutical fluid. The vessel 200 may be translucent or opaque, such that a user can see a fluid contained therein. This may be particularly useful when the fluid must be visually inspected or volumetrically measured. In this regard, the vessel 200 can include indicia 202 along a side wall thereof. The indicia 202 can allow a user to quickly measure the volume of a fluid within the vessel 200. This can assist during mixing or process steps of production.

Moreover, in particular embodiments, the vessel 200 can comprise a material adapted to withstand, i.e., maintain operational functionality, at temperatures of greater than 200° F., such as greater than 220° F., greater than 250° F., greater than 260° F., greater than 270° F., or even greater than 280° F.

Varying sized vessels 200 can be utilized with the tray 100. For example, the vessel 200 can be adapted to contain at least 1 Liter (L) of fluid, such as at least 2 L of fluid, at least 3 L of fluid, at least 5 L of fluid, or even at least 10 L of fluid. Markings 204 can indicate to a user the volumetric capacity of the vessel 200.

A cap 206 can be installed on an opening of the vessel 200. In particular embodiments, the cap 206 can threadably engage with a complementary threaded portion disposed at the opening of the vessel 200. In alternate embodiments, the cap 206 can be clamped, snapped, adhered, mechanically deformed (e.g., pinched), bayonet connected, or attached to the opening of the vessel 200 by any similar process or combination thereof.

In certain embodiments, the vessel 200 can include an air port 208. The air port 208 can permit entrance of an ambient fluid, e.g., room air, into the vessel 200. This may permit pressure equalization within the vessel, allowing quicker filling and unfilling thereof. A filter can be disposed along each air port. The filter can prevent ingress of contaminants into the vessel.

One of ordinary skill in the art will recognize that a plurality of vessels 200 can be disposed within the recess(es) 130 or 144 of the tray 100. In certain embodiments, each vessel 200 utilized with the tray 100 at a particular time can be identical, e.g., each vessel may have the same dimensions and may comprise the same material.

Each of the plurality of vessels 200 can be connected to a fluid supply system by a tubing system 300 including a tube 302 and a plurality of sub-tubes 304. The tube 302 can extend along the channel 114. The sub-tubes 304 can be disposed between the vessels 200 and the tube 302, thereby putting the tube 302 in fluid communication with the vessels 200.

In particular embodiments, one or more of the tube 302 and sub-tubes 304 can be positioned within a clamp 148 disposed along the tray 100. In a particular embodiment, the clamp 148 can extend outward from a surface of the tray 100. In another embodiment, the clamp can be an independent component engaged with the tube 302 or sub-tube 304. The clamp 148 can receive the tube 302 or sub-tube 304 along an opening or slit therein. When engaged, the clamp 148 can block fluid flow through the tube 302 or sub-tube 304. When disengaged, the clamp 148 can permit fluid flow through the tube 302 or sub-tube 304. In further embodiments, the tray 100 can include a plurality of clamps, each clamp adapted to receive a same or different tube 302 or sub-tube 304. In a certain embodiment, a ratio of clamps to vessels can be at least 1:1, such as at least 2:1, or even at least 3:1. In yet another embodiment, a ratio of clamps to tubes and sub-tubes can be at least 1:1, such as at least 2:1, or even at least 3:1.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. An article adapted for use with biological or biologically active substances, the article comprising:
  a tray comprising:
    a base having a top surface; and
    a manifold extending from the top surface of the base, the manifold comprising a sidewall and an upper surface, the upper surface further comprising a channel,
    wherein, when viewed from the top surface, the base has an area, $A_B$, the upper surface of the manifold has an area $A_M$, and $A_B > A_M$, and wherein the base is adapted to support a plurality of vessels each adapted to contain a fluid.

Item 2. An article adapted for use with biological or biologically active substances, the article comprising:
  a tray comprising:
    a base having a top surface; and
    a manifold extending from the top surface of the base, the manifold comprising a sidewall and an upper surface, the upper surface further comprising a channel,
    wherein, when viewed from the top surface, the base has an area, $A_B$, the upper surface of the manifold has an area $A_M$, and $A_B > A_M$; and
  a plurality of vessels each adapted to contain a fluid, the plurality of vessels disposed on the top surface of the base.

Item 3. An article adapted for use with biological or biologically active substances, the article comprising:
  a tray comprising:
    a base having a top surface; and
    a manifold extending from the top surface of the base, the manifold comprising a sidewall and an upper surface, the upper surface further comprising a channel,
    wherein, when viewed from the top surface, the base has an area, $A_B$, the upper surface of the manifold has an area $A_M$, and $A_B > A_M$;
  a plurality of vessels each adapted to contain a fluid, the plurality of vessels disposed on the top surface of the base; and
  a tube at least partially recessed in the channel of the tray and extending to at least one of the plurality of vessels, the tube adapted to transport a fluid to the at least one of the plurality of vessels, away from the at least one of the plurality of vessels, or a combination thereof.

Item 4. The article according to any one of the preceding items, wherein the sidewall of the manifold is generally frustoconical.

Item 5. The article according to any one of the preceding items, wherein the manifold extends from the base a distance, $D_M$, wherein the base has a maximum thickness, $T_B$, and wherein $D_M$ is greater than $T_B$, such as $D_M$ is greater than 1.25 $T_B$, such as greater than 1.5 $T_B$, greater than 1.75 $T_B$, or even greater than 2.0 $T_B$.

Item 6. The article according to item 5, wherein $D_M$ is less than 100 $T_B$, such as less than 50 $T_B$, less than 10 $T_B$, less than 5 $T_B$, or even less than 3 $T_B$.

Item 7. The article according to any one of the preceding items, wherein, when viewed from the upper surface, the manifold has a length, $L_M$, and a width, $W_M$, and wherein $L_M$ is greater than $W_M$, such as $L_M$ is greater than 1.1 $W_M$, greater than 1.2 $W_M$, greater than 1.5 $W_M$, greater than 1.75 $W_M$, or even greater than 2.0 $W_M$.

Item 8. The article according to item 7, wherein $L_M$ is less than 5.0 $W_M$, such as less than 4.0 $W_M$, or even less than 3.0 $W_M$.

Item 9. The article according to any one of items 7 and 8, wherein the channel extends along the length of the manifold.

Item 10. The article according to any one of items 7-9, wherein the channel is oriented in a direction substantially parallel with the length of the manifold.

Item 11. The article according to any one of the preceding items, wherein the channel has a depth, $D_C$, as measured from the upper surface of the manifold, wherein the manifold extends from the base a distance, $D_M$, and wherein $D_C$ is less than $D_M$.

Item 12. The article according to item 11, wherein $D_C$ is no greater than 0.99 $D_M$, such as no greater than 0.75 $D_M$, no greater than 0.5 $D_M$, no greater than 0.25 $D_M$, or even no greater than 0.1 $D_M$.

Item 13. The article according to any one of the preceding items, wherein the channel has a width, $W_C$, as measured along the upper surface of the manifold, wherein the upper surface of the manifold has a width, $W_M$, and wherein $W_C$ is less than $W_M$.

Item 14. The article according to item 13, wherein $W_C$ is no greater than 0.99 $W_M$, such as no greater than 0.75 $W_M$, no greater than 0.5 $W_M$, no greater than 0.25 $W_M$, or even no greater than 0.1 $W_M$.

Item 15. The article according to any one of the preceding items, wherein the channel is adapted to receive at least a portion of a tube.

Item 16. The article according to any one of the preceding items, wherein the channel is adapted to receive all of a tube.

Item 17. The article according to any one of the preceding items, wherein the upper surface of the manifold further comprises a plurality of sub-channels.

Item 18. The article according to item 17, wherein each of the sub-channels is oriented along a line that intersects the channel.

Item 19. The article according to any one of items 17 and 18, wherein each of the sub-channels is oriented perpendicular to the channel.

Item 20. The article according to any one of items 17-19, wherein each of the sub-channels is adapted to receive at least a portion of a sub-tube.

Item 21. The article according to any one of items 17-20, wherein each of the sub-channels is adapted to receive all of a sub-tube.

Item 22. The article according to any one of items 17-21, wherein the sub-channels each have a depth, $D_{SC}$, wherein the channel has a depth, $D_C$, and wherein $D_{SC}$ is equal to $D_C$.

Item 23. The article according to any one of items 17-21, wherein the sub-channels each have a depth, $D_{SC}$, wherein the channel has a depth, $D_C$, and wherein $D_C$ is greater than $D_{SC}$.

Item 24. The article according to item 23, wherein $D_C$ is at least 1.01 $D_{SC}$, such as at least 1.1 $D_{SC}$, at least 1.2 $D_{SC}$, at least 1.3 $D_{SC}$, or even at least 1.5 $D_{SC}$.

Item 25. The article according to any one of items 23 and 24, wherein $D_C$ is no greater than 10 $D_{SC}$, such as no greater than 9 $D_{SC}$, no greater than 8 $D_{SC}$, no greater than 5 $D_{SC}$, or even no greater than 2 $D_{SC}$.

Item 26. The article according to any one of items 17-25, wherein the sub-channels have a width, $W_{SC}$, wherein the channel has a width, $W_C$, and wherein $W_{SC}$ is equal to $W_C$.

Item 27. The article according to any one of items 17-25, wherein the sub-channels have a width, $W_{SC}$, wherein the channel has a width, $W_C$, and wherein $W_{SC}$ is less than $W_C$.

Item 28. The article according to item 27, wherein $W_{SC}$ is no greater than 0.99 $W_C$, such as no greater than 0.90 $W_C$, or even no greater than 0.75 $W_C$.

Item 29. The article according to any one of the preceding items, further comprising a reinforcement member disposed along the sidewall of the manifold.

Item 30. The article according to any one of the preceding items, further comprising a plurality of first reinforcement members disposed along the sidewall of the manifold and a plurality of second reinforcement members disposed along the sidewall of the manifold, wherein the first reinforcement members have a first height, wherein the second reinforcement members have a second height, and wherein the first height is less than the second height.

Item 31. The article according to any one of the preceding items, wherein the tray further comprises a handle.

Item 32. The article according to item 31, wherein the handle is disposed on the manifold.

Item 36. The article according to any one of items 31 or 32, wherein the handle is disposed on the sidewall of the manifold.

Item 34. The article according to item 31, wherein the handle is disposed on the base.

Item 35. The article according to any one of items 31-34, wherein the handle comprises a plurality of handles.

Item 36. The article according to item 35, wherein the plurality of handles are disposed at opposite ends of the manifold.

Item 37. The article according to any one of items 31-36, wherein the handle is monolithic with the tray.

Item 38. The article according to any one of items 31-36, wherein the handle is attached to the tray by a threaded fastener.

Item 39. The article according to any one of items 31-36, and 38, wherein the handle is attached to the tray by an adhesive.

Item 40. The article according to any one of items 31-37, wherein the handle comprises a recess extending into the tray.

Item 41. The article according to any one of the preceding items, wherein the tray comprises a recess adapted to receive at least one vessel, and wherein the recess extends from a top surface of the base in a direction toward a bottom surface of the base.

Item 42. The article according to item 41, wherein the recess is adapted to receive a plurality of vessels and individually support at least one vessel of the plurality of vessels.

Item 43. A article adapted for use in the production of pharmaceuticals, the article comprising a tray having a recess, the recess adapted to receive a plurality of vessels and individually support at least one vessel of the plurality of vessels.

Item 44. The article according to any one of items 41-43, wherein the recess defines a sidewall and a bottom wall.

Item 45. The article according to item 44, wherein, when viewed from a top view, the sidewall of the recess defines an undulating profile.

Item 46. The article according to any one of items 44 and 45, wherein, when viewed from a top view, the sidewall of the recess defines a maximum width, as measured between opposite sides of the recess, and a minimum width, as measured between opposite sides of the recess, and wherein the maximum width of the sidewall is at least 1.1 times the minimum width of the sidewall, such as at least 1.25 times the minimum width of the sidewall, or even 1.75 times the minimum width of the sidewall.

Item 47. The article according to any one of items 41-46, wherein the recess defines a plurality of discrete containment regions, each discrete containment region adapted to receive one vessel.

Item 48. The article according to item 47, wherein each discrete containment region is adapted to support and provide radial stability to one vessel.

Item 49. The article according to any one of items 47 and 48, wherein, when viewed from a top view, adjacent containment regions of the plurality of discrete containment regions are in open communication with each other.

Item 50. The article according to any one of items 47-49, wherein a first vessel is disposed in a first discrete containment region, wherein a second vessel is disposed in a second discrete containment region adjacent to the first discrete containment region, and wherein a closest distance between the first and second vessels is no greater than 1 inch, such as no greater than 0.75 inches, no greater than 0.5 inches, or even no greater than 0.25 inches.

Item 51. The article according to item 50, wherein the first and second vessels are in contact.

Item 52. The article according to any one of items 41-51, wherein the recess comprises two recesses.

Item 53. The article according to any one of items 41-52, wherein the recess has a depth, $D_R$, as measured from the top surface of the base, wherein the base has a thickness, $T_B$, and wherein $D_R$ is less than $T_B$.

Item 54. The article according to item 53, wherein $D_R$ is less than 0.99 $T_B$, such as less than 0.95 $T_B$, less than 0.90 $T_B$, or even less than 0.75 $T_B$.

Item 55. The article according to any one of items 53 and 54, wherein $D_R$ is no less than 0.05 $T_B$, such as no less than 0.1 $T_B$, or even no less than 0.25 $T_B$.

Item 56. The article according to any one of items 41-55, wherein the recess has a chamfered lip.

Item 57. The article according to any one of the preceding items, wherein the tray comprises a polymer.

Item 58. The article according to any one of the preceding items, wherein the tray comprises HDPE.

Item 59. The article according to any one of the preceding items, wherein the tray further comprises an outer coating.

Item 60. The article according to item 59, wherein the outer coating comprises a polymer.

Item 61. The article according to any one of items 59 and 60, wherein the outer coating comprises an elastomer.

Item 62. The article according to any one of the preceding items, wherein the tray is monolithic.

Item 63. The article according to any one of the preceding items, wherein the tray is injection molded.

Item 64. The article according to any one of the preceding items, wherein the tray is thermoformed.

Item 65. The article according to any one of the preceding items, wherein the tray is adapted to withstand temperatures of greater than 200° F., such as greater than 220° F., greater than 250° F., greater than 260° F., or even greater than 270° F.

Item 66. The article according to any one of the preceding items, wherein the tray is a single use tray.

Item 67. The article according to any one of the preceding items, wherein the tray is essentially sterile.

Item 68. The article according to any one of the preceding items, wherein the tray is sterile.

Item 69. The article according to any one of the preceding items, wherein the tray further comprises a pump.

Item 70. The article according to any one of the preceding items, wherein the tray further comprises an integral pump, the integral pump attached to the tray.

Item 71. The article according to any one of the preceding items, wherein the tray further comprises a drainage member adapted to remove a fluid from a vessel disposed on the tray.

Item 72. The article according to item 71, wherein the drainage member comprises:
a drainage hose extending from the vessel; and
a pump adapted to bias a fluid through the hose in a direction away from the vessel.

Item 73. The article according to any one of the preceding items, wherein the tray further comprises a clamp adapted to hold a tube and selectively terminate a fluid flow through the tube upon operative engagement.

Item 74. The article according to any one of the preceding items, wherein the tray further comprises a plurality of clamps, each adapted to hold a tube and selectively terminate a fluid flow through the tube, wherein a ratio of clamps to vessels is 1:1.

Item 75. The article according to any one of the preceding items, wherein the tray is adapted to receive and support at least one vessel.

Item 76. The article according to any one of the preceding items, wherein at least a portion of at least one of the vessels is frustoconical.

Item 77. The article according to any one of the preceding items, wherein at least a portion of at least one of the vessels is cylindrical.

Item 78. The article according to any one of the preceding items, wherein, when viewed from a top view, at least a portion of at least one of the vessels is polygonal.

Item 79. The article according to any one of the preceding items, wherein each vessel is identical.

Item 80. The article according to any one of the preceding items, wherein each vessel is adapted to contain a fluid of no less than 1 liter (L), such as no less than 2 L, no less than 5 L, or even no less than 10 L.

Item 81. The article according to any one of the preceding items, wherein at least one of the vessels has a cap, the cap adapted to be threadably engaged with the at least one vessel.

Item 82. The article according to any one of the preceding items, wherein at least one of the vessels comprise a polymer.

Item 83. The article according to any one of the preceding items, wherein at least one of the vessels comprises an inert polymer.

Item 84. The article according to any one of the preceding items, wherein all of the vessels comprise an inert polymer.

Item 85. The article according to any one of the preceding items, wherein the vessels are adapted to withstand temperatures of greater than 200° F., such as greater than 220° F., greater than 250° F., greater than 260° F., or even greater than 270° F.

Item 86. The article according to any one of the preceding items, wherein at least one of the vessels is translucent such that an operator can see a fluid contained within the vessel.

Item 87. The article according to any one of the preceding items, wherein at least one of the vessels includes indicia allowing a user to determine a volume of fluid contained within the vessel.

Item 88. The article according to any one of the preceding items, wherein at least one of the vessels includes a marking indicating a volumetric capacity of the vessel.

Item 89. The article according to any one of the preceding items, wherein each vessel further comprises an air port, and wherein the air port is adapted to permit pressure equalization within the vessel during filling and draining.

Item 90. The article according to item 89, wherein each air port further comprises a filter adapted to prevent ingress of a contaminant into the vessel.

Item 91. The article according to any one of the preceding items, wherein the vessels are adapted to contain a pharmaceutical fluid.

The above-disclosed subject matter is to be considered illustrative, and not restrictive, and the claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

In addition, in the foregoing detailed description, various features can be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter can be directed to less than all features of any of the disclosed embodiments. Thus, the following claims are incorporated into the detailed description, with each claim standing on its own as defining separately claimed subject matter.

What is claimed is:

1. An article adapted for use with biological or biologically active substances, the article comprising:
   a tray comprising:
      a base having a top surface; and
      a manifold extending from the top surface of the base, the manifold comprising a sidewall and an upper surface, the upper surface further comprising a channel,
      wherein, when viewed from the top surface, the base has an area, $A_B$, the upper surface of the manifold has an area $A_M$, and $A_B > A_M$;
   a plurality of vessels each adapted to contain a fluid, the plurality of vessels disposed on the top surface of the base; and
   a tube at least partially recessed in the channel of the tray and extending to at least one of the plurality of vessels, the tube adapted to transport a fluid to the at least one of the plurality of vessels, away from the at least one of the plurality of vessels, or a combination thereof.

2. The article according to claim 1, wherein the channel extends along the length of the manifold.

3. The article according to claim 1, wherein the channel has a depth, $D_C$, as measured from the upper surface of the manifold, wherein the manifold extends from the base a distance, $D_M$, and wherein $D_C$ is less than $D_M$.

4. The article according to claim 1, wherein the tray further comprises a handle, and wherein the handle is monolithic with the tray.

5. The article according to claim 1, wherein the upper surface of the manifold further comprises a plurality of sub-channels extending from the channel.

6. The article according to claim 5, wherein each of the sub-channels is oriented perpendicular to the channel.

7. The article according to claim 5, wherein each of the sub-channels is adapted to receive at least a portion of a sub-tube.

8. The article according to claim 5, wherein each of the sub-channels is adapted to receive all of a sub-tube.

9. The article according to claim 1, wherein the tray comprises a recess adapted to receive at least one vessel, and wherein the recess extends from a top surface of the base in a direction toward a bottom surface of the base.

10. The article according to claim 9, wherein the recess defines a plurality of discrete containment regions, each discrete containment region adapted to receive and individually support one vessel.

11. The article according to claim 10, wherein, when viewed from a top view, adjacent containment regions of the plurality of discrete containment regions are in open communication with each other.

12. The article according to claim 9, wherein, when viewed from a top view, a sidewall of the recess defines a maximum width, as measured between opposite sides of the recess, and a minimum width, as measured between opposite sides of the recess, and wherein the maximum width of the sidewall is at least 1.1 times the minimum width of the sidewall.

13. The article according to claim 1, wherein the sidewall of the manifold is generally frustoconical.

14. The article according to claim 1, wherein the manifold extends from the base a distance, $D_M$, wherein the base has a maximum thickness, $T_B$, and wherein $D_M$ is greater than $T_B$.

15. The article according to claim 14, wherein $D_M$ is less than 100 $T_B$.

16. The article according to claim 1, when viewed from the upper surface, the manifold has a length, $L_M$, and a width, $W_M$, and wherein $L_M$ is greater than $W_M$.

17. The article according to claim 16, wherein $L_M$ is less than 5.0 $W_M$.

18. The article according to claim 1, wherein the channel is oriented in a direction substantially parallel with the length of the manifold.

19. The article according to claim 1, wherein the channel is adapted to receive all of a tube.

20. The article according to claim 1, further comprising a reinforcement member disposed along the sidewall of the manifold.

* * * * *